United States Patent
Yamamoto et al.

(10) Patent No.: US 6,858,559 B2
(45) Date of Patent: Feb. 22, 2005

(54) ASYMMETRIC COPPER COMPLEX AND CYCLOPROPANATION REACTION USING THE SAME

(75) Inventors: Michio Yamamoto, Otsu (JP); Gohfu Suzukamo, Suita (JP); Makoto Itagaki, Takatsuki (JP)

(73) Assignee: Sumitomo Chemical Company, Limited, Osaka (JP)

( * ) Notice: Subject to any disclaimer, the term of this patent is extended or adjusted under 35 U.S.C. 154(b) by 147 days.

(21) Appl. No.: 10/128,237

(22) Filed: Apr. 24, 2002

(65) Prior Publication Data

US 2002/0177718 A1 Nov. 28, 2002

(30) Foreign Application Priority Data

Apr. 27, 2001 (JP) .......................................... 2001-132016

(51) Int. Cl.$^7$ ................................................. B01J 31/00
(52) U.S. Cl. ........................ 502/165; 556/110; 548/101
(58) Field of Search .......................... 502/165; 556/110; 548/101

(56) References Cited

U.S. PATENT DOCUMENTS

| | | | |
|---|---|---|---|
| 4,033,976 A | * | 7/1977 | Briedis et al. ............... 548/101 |
| 5,298,623 A | | 3/1994 | Masamune et al. |
| 6,011,169 A | | 1/2000 | Itagaki et al. |
| 6,072,081 A | * | 6/2000 | Itagaki et al. ................ 562/506 |
| 6,664,350 B1 | * | 12/2003 | Haddleton et al. ........... 526/135 |
| 2004/0133009 A1 | * | 7/2004 | Schottek et al. ............. 548/101 |

FOREIGN PATENT DOCUMENTS

| | | |
|---|---|---|
| EP | 0 895 992 A2 | 2/1999 |
| HU | 210 648 B | 9/1983 |

OTHER PUBLICATIONS

Takei, Surface Technology, vol. 22, pp. 343–352 (1984).*
Hungarian Patent Office Novelty Search Report Appln No. P0201357.
D.A. Evans et al., J. Am. Chem. Soc., 113, 726–728 (1991) XP–002205122.
K. Alexander et al., Tetrahedron Letters, 41, 7135–7138 (2000).
R. Tokunoh et al., Tetrahedron Letters, 37(14) 2449–2452 (1996).
A.M.P. Koskinen et al., J. Org. Chem., 58, 4479–4480 (1993) XP–001088091.
Tetrahedron Letters, 31 (42) pp. 6005–6008 (1990).
Tetrahedron Letters, 32 (50) pp. 7373–7376 (1991).

* cited by examiner

*Primary Examiner*—Mark L. Bell
*Assistant Examiner*—J. Pasterczyk
(74) *Attorney, Agent, or Firm*—Birch, Stewart, Kolasch & Birch, LLP

(57) ABSTRACT

Disclosed is an asymmetric copper catalyst composition comprising, as components, (a) an optically active bisoxazoline compound of formula (1):

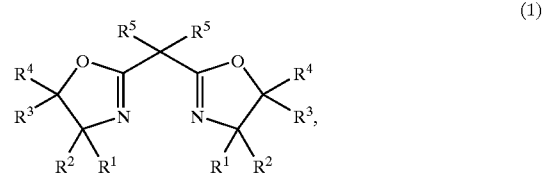

(1)

wherein
$R^1$ and $R^2$ are different and each represents a hydrogen atom, an alkyl group, a cycloalkyl group, or a phenyl or aralkyl group which may be substituted, $R^3$ and $R^4$ each represents a hydrogen atom, an alkyl group, a cycloalkyl group, or a phenyl or aralkyl group which may be substituted, or $R^3$ and $R^4$ may be bonded to each other to form a $C_{3-5}$ cyclic alkylene group, $R^5$ represents a hydrogen atom or a $C_{1-6}$ alkyl group, or the two $R^5$ groups may be bonded to each other to represent a $C_{3-5}$ cyclic alkylene group, (b) a monovalent or divalent copper compound, and
(c) a strong acid or a Lewis acid or a mixture thereof, and a process for producing an optically active cyclopropanecarboxylate using the same.

13 Claims, No Drawings

ASYMMETRIC COPPER COMPLEX AND CYCLOPROPANATION REACTION USING THE SAME

FIELD OF THE INVENTION

This invention relates to an asymmetric copper complex comprising, as components, an optically active bisoxazoline compound, a copper compound and a strong acid or a Lewis acid or a mixture thereof, a process for producing the same and a process for producing an optically active cyclopropane compound by using the same as a catalyst.

BACKGROUND OF THE INVENTION

An optically active cyclopropanecarboxylate is an important compound as an intermediate for the production of pharmaceuticals and agrochemicals. For example, (+)-2,2-dimethyl-3-(2-methyl-1-propenyl)cyclopropanecarboxylic acid known as chrysanthemum-monocarboxylic acid constitutes an acid component of synthetic pyrethroid type insecticides. (+)-2,2-Dimethylcyclopropanecarboxylic acid is known to be useful as an intermediate for synthesis of β-lactam type antibiotics.

Conventional methods known to produce the optically active cyclopropanecarboxylic acid derivatives directly by synthetic means are a method of reacting a prochiral olefin with a diazoacetate in the presence of an asymmetric copper complex using optically active bis[2-(4,5-diphenyl-1,3-oxazolynyl)]methane as a ligand (Tetrahedron Lett., 32, 7373, 1991 etc.).

These methods, however, were not always satisfactory as an industrial production method in that complicated procedures were required to produce the copper complex and handling thereof was not always easy because of its poor stability.

SUMMARY OF THE INVENTION

According to the present invention, an asymmetric copper complex catalyst, which is useful for the production of an optically active cyclopropanecarboxylate can be readily produced from readily available inexpensive copper compounds.

The present invention provides:

1. an asymmetric copper complex, comprising, as components,
    (a) an optically active bisoxazoline compound of formula (1):

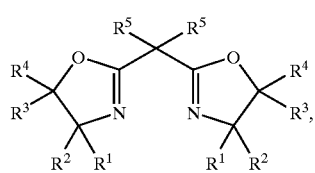

(1)

wherein
  $R^1$ and $R^2$ are different and each represent a hydrogen atom, an alkyl group, a cycloalkyl group, or a phenyl or aralkyl group which may be substituted;
  $R^3$ and $R^4$ each represent a hydrogen atom, an alkyl group, a cycloalkyl group, or a phenyl or aralkyl group which may be substituted, or $R^3$ and $R^4$ are bonded to each other to form a $C_{3-5}$ cyclic alkylene group; and
  $R^5$ represents a hydrogen atom or a $C_{1-6}$ alkyl group, or the two $R^5$ groups are bonded to each other to represent a $C_{3-6}$ cyclic alkylene group;
    (b) a monovalent or divalent copper compound; and
    (c) a strong acid or a Lewis acid or a mixture thereof;
2. a process for producing the asymmetric copper complex as defined above, which comprises reacting
    (a) an optically active bisoxazoline compound of formula (1) as defined above,
    (b) a monovalent or divalent copper compound, and
    (c) a strong acid or a Lewis acid or a mixture thereof; and
3. a process for producing an optically active cyclopropanecarboxylic acid ester, which comprises reacting a prochiral olefin compound with diazoacetate in the presence of the asymmetric copper complex as defined above.

DETAILED DESCRIPTION OF THE INVENTION

A description will be first made to the substituent groups represented by $R^1$ to $R^{10}$ including those present on the substituent groups.

In the present specification, examples of the alkyl group include, for example, a $C_{1-8}$ alkyl group, and specific examples thereof include, methyl, ethyl, n-propyl, i-propyl, n-butyl, s-butyl, i-butyl, t-butyl, n-pentyl, i-pentyl, t-pentyl, neo-pentyl, n-hexyl, s-hexyl, i-hexyl, n-heptyl, n-octyl, or the like.

Examples of the $C_{1-6}$ alkyl group represented by $R^5$ include, for example, from methyl to i-hexyl groups in the above described specific examples.

Examples of the cycloalkyl group include, for example, a $C_{3-10}$ cycloalkyl group, and specific examples thereof include, cyclopropyl, cyclobutyl, cyclopentyl, cyclohexyl, cycloheptyl, cyclooctyl, cyclononyl, cyclodecyl and menthyl.

The $C_{3-6}$ alkylene group means a trimethylene, tetramethylene, pentamethylene, or hexamethylene group.

Examples of the alkoxy group include, for example, a $C_{1-8}$ alkoxy group, and specific examples thereof include, methoxy, ethoxy, n-propoxy, i-propoxy, n-butoxy, s-butoxy, i-butoxy, t-butoxy, n-pentyloxy, i-pentylxoy, t-pentyloxy, neo-pentyloxy, n-hexyloxy, s-hexyloxy, i-hexyloxy, n-heptyloxy, n-octyloxy, or the like.

The halogen atom means a fluorine, chlorine, bromine, or iodine atom.

Examples of the aralkyl group include, for example, $C_{7-12}$ aralkyl group, and specific examples thereof include, for example, benzyl, 1-, or 2-phenethyl, 1-, or 2-naphthylmethyl group, naphthylethyl, and the like.

The phenyl or aralkyl group which may be substituted, represented by any one of $R^1$ to $R^4$, include a phenyl or aralkyl group (e.g. $C_{7-12}$ aralkyl group as specified above) which may be substituted with a halogen atom, an alkyl (e.g., $C_{1-8}$ alkyl group as specified above) or alkoxy group (e.g, $C_{1-8}$ alkoxy group as specified above).

Examples of the optically active bisoxazoline compounds of formula (1) include, for example,
2,2'-methylenebis[(4R)-4-phenyl-2-oxazoline],
2,2'-methylenebis[(4R)-4-isopropyl-2-oxazoline],
2,2'-methylenebis[(4R)-4-t-butyl-2-oxazoline],
2,2'-methylenebis[(4R)-4-benzyl-2-oxazoline],
2,2'-methylenebis[(4R,5R)-4-methyl-5-phenyl-2-oxazoline],
2,2'-methylenebis[(4R,5S)-4-benzyl-5-phenyl-2-oxazoline], 2,2'-methylenebis[(4R,5S)-4,5-diphenyl-2-oxazoline],
2,2'-methylenebis[(4R)-4-phenyl-5,5-dimethyl-2-oxazoline],
2,2'-methylenebis[(4R)-4-phenyl-5,5-diethyl-2-oxazoline],
2,2'-methylenebis[(4R)-4-phenyl-5,5-di-n-propyl-2-oxazoline],
2,2'-methylenebis[(4R)-4-phenyl-5,5-di-i-propyl-2-oxazoline],
2,2'-methylenebis[(4R)-4-phenyl-5,5-dicyclohexyl-2-oxazoline],
2,2'-methylenebis[(4R)-4-phenyl-5,5-diphenyl-2-oxazoline],
2,2'-methylenebis[(4R)-4-phenyl-5,5-di-(2-methylphenyl)-2-oxazoline],
2,2'-methylenebis[(4R)-4-phenyl-5,5-di-(3-methylphenyl)-2-oxazoline],
2,2'-methylenebis[(4R)-4-phenyl-5,5-di-(4-methylphenyl)-2-oxazoline],
2,2'-methylenebis[(4R)-4-phenyl-5,5-di-(2-methoxyphenyl)-2-oxazoline],
2,2'-methylenebis[(4R)-4-phenyl-5,5-di-(3-methoxyphenyl)-2-oxazoline],
2,2'-methylenebis[(4R)-4-phenyl-5,5-di-(4-methoxyphenyl)-2-oxazoline],
2,2'-methylenebis[spiro{(4R)-4-phenyl-2-oxazoline-5,1'-cyclobutane}],
2,2'-methylenebis[spiro{(4R)-4-phenyl-2-oxazoline-5,1'-cyclopentane}],
2,2'-methylenebis[spiro{(4R)-4-phenyl-2-oxazoline-5,1'-cyclohexane}],
2,2'-methylenebis[spiro{(4R)-4-phenyl-2-oxazoline-5,1'-cycloheptane}],
2,2'-isopylidenebis[(4R)-4-phenyl-2-oxazoline],
2,2'-isopylidenebis[(4R)-4-isopropyl-2-oxazoline],
2,2'-isopylidenebis[(4R)-4-t-butyl-2-oxazoline],
2,2'-isopylidenebis[(4R)-4-benzyl-2-oxazoline],
2,2'-isopylidenebis[(4R,5R)-4-methyl-5-phenyl-2-oxazoline],
2,2'-isopylidenebis[(4R,5S)-4,5-diphenyl-2-oxazoline],
2,2'-isopylidenebis[(4R,5S)-4-benzyl-5-phenyl-2-oxazoline],
2,2'-isopylidenebis[(4R)-4-phenyl-5,5-dimethyl-2-oxazoline],
2,2'-isopylidenebis[(4R)-4-phenyl-5,5-diethyl-2-oxazoline],
2,2'-isopylidenebis[(4R)-4-phenyl-5,5-di-n-propyl-2-oxazoline],
2,2'-isopylidenebis[(4R)-4-phenyl-5,5-di-i-propyl-2-oxazoline],
2,2'-isopylidenebis[(4R)-4-phenyl-5,5-dicyclohexyl-2-oxazoline],
2,2'-isopylidenebis[(4R)-4-phenyl-5,5-di-phenyl-2-oxazoline],
2,2'-isopylidenebis[(4R)-4-phenyl-5,5-di-(2-methylphenyl)-2-oxazoline],
2,2'-isopylidenebis[(4R)-4-phenyl-5,5-di-(3-methylphenyl)-2-oxazoline],
2,2'-isopylidenebis[(4R)-4-phenyl-5,5-di-(4-methylphenyl)-2-oxazoline],
2,2'-isopylidenebis[(4R)-4-phenyl-5,5-di-(2-methoxyphenyl)-2-oxazoline], and the like.

The bisoxazoline compounds include bisoxazoline compounds having an absolute configuration opposite to that of the compounds described above.

The monovalent or divalent copper compound includes a copper salt, which typically comprises a monovalent or divalent copper ion and a balancing anion(s), and an oxide of monovalent or divalent copper.

Examples of the monovalent or divalent copper compound include, for example, copper carboxylates having 2 to 15 carbon atoms such as copper acetate, copper octanoate, copper naphthenate, etc., and copper acetylacetonate; copper halide such as copper chloride, copper bromide or the like; copper sulfonate such as copper methanesulfonate or the like, copper carbonate; copper hydroxide; copper oxide and the like.

The strong acid is preferably an acid having stronger acidity than the acid of the balancing counter anion of the above-described copper compound. As for the acidity, Hammett value "Ho" or pK value may be referred to (R. A. Cox, K. Yates, Can. J.Chem., 61, 2225 (1983) and the whole disclosure of which is incorporated herein by reference). For example, an acid stronger than acetic acid is preferably used together with copper acetate, and an acid that is stronger than hydrochloric acid is used with copper chloride.

Alternatively, preferred strong acid is a strong acid of which acidity falls within a range of Hammett value "Ho" of about –10 to about –50, or pK value range of about 3 or less.

Specific examples of the preferred strong acid include, for example, trifluoromethanesulfonic acid, fluorosulfonic acid, chlorosulfonic acid, hydrogen fluoride, fuming sulfuric acid, conc. sulfuric acid, Nafion (trade name) and the like.

Examples of the Lewis acid include, for example, boron trifluoride, tantalum pentafluoride, niobium pentafluoride, titanium tetrafluoride, phosphorus pentafluoride, antimony pentafluoride, arsenic pentafluoride, tungsten hexafluoride, antimony trifluoride, aluminum trifluoride, tris-(pentafluorophenyl)aluminium or the like, and Lewis acid complex salts such as a boron trifluoride-diethyl ether complex salt, a boron trifluoride-methanol complex salt, a boron trifluoride-phenol complex salt, and the like.

The strong acid can be used alone or in combination with a Lewis acid. Preferred examples of the mixtures (combinations) of a strong acid and a Lewis acid include, for example, a mixture of boron trifluoride and hydrogen fluoride, a mixture of antimony pentafluoride and hydrogen fluoride, a mixture of phosphorus pentafluoride and hydrogen fluoride, a mixture of antimony pentafluoride and fluorosulfonic acid, a mixture of antimony pentafluoride and trifluoromethanesulfonic acid and the like.

The asymmetric copper complex is usually produced by mixing the components typically in a solvent, and any combination of the components recited under (a), (b) and (c) above may be selected and are made to be contacted with each other, and the remaining component(s) can be further added thereto, thus the order of addition of the components are not limited.

For example, the production of the asymmetric copper complex may be conducted by any one of the following methods:

a method wherein the above-described copper compound is reacted with the optically active bisoxazoline compound of formula (1) and then the strong acid is added thereto;

a method wherein the copper compound is reacted with the strong acid and then the optically active bisoxazoline compound of formula (1) is added and mixed therewith; or a method wherein the optically active bisoxazoline compound of formula (1) is mixed with the strong acid and then the above-described copper compound is added thereto.

Preferred is a method wherein the copper compound is reacted with the optically active bisoxazoline compound of formula (1) to produce a copper complex, and thereafter the resulting copper complex is reacted with the strong acid or Lewis acid or a mixture thereof.

Any suitable organic solvent can be used in the present production method. A solvent that can form a catalyst solution of the resulting asymmetric copper complex in a solvent is preferably used.

Examples of the solvent that may be used include, for example, an aromatic hydrocarbon such as toluene, xylene or the like, an aliphatic hydrocarbon such as hexane, cyclohexane, heptane or the like, a halogenated hydrocarbon such as chloroform, dichloroethane, monochlorobutane or the like, an ester such as methyl acetate, ethyl acetate, ethyl propionate or the like, or a mixture thereof.

The optically active bisoxazoline compound of formula (1) is used usually in an amount of about 0.9 to 2 moles per mol of the monovalent or divalent copper compound, and the strong acid or Lewis acid or a mixture thereof is used usually in an amount of about 0.3 to 5 moles per mol of the monovalent or divalent copper compound.

The mixing of the respective components is usually conducted at a temperature range of from room temperature to the boiling point of the solvent, and preferably in the range of about 0 to 60° C. for a suitable period of time.

Preferably, the asymmetric copper complex may be used in a solution form, and particularly purification thereof is not required, but the complex can also be used after isolation and purification by removing the solvent. The asymmetric copper complex catalyst can be conveniently used as such in a solution form so as to continuously feed the catalyst in a continuous reaction process. Alternatively, the asymmetric copper complex, which is not a solution, (e.g, in a form of slurry or solid) may also be used, as a catalyst, in a reaction in which a slurry reaction mass is being stirred or in a continuous reaction using a packed tower of solid catalyst.

Hereinafter described is the method for producing an optically active cyclopropanecarboxylic acid ester, which comprises reacting a prochiral olefin with a diazoacetate in the presence of the asymmetric copper complex catalyst.

Examples of the prochiral olefin include a prochiral olefin of formula (2):

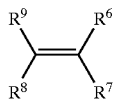

(2)

$R^6$, $R^7$, $R^8$ and $R^9$ each represent a hydrogen atom; a halogen atom;

an alkyl group which may be substituted with a halogen atom or an alkoxy group;

an alkenyl group which may be substituted with a halogen atom, an alkoxy group, an alkoxycarbonyl group or a halogenated alkoxycarbonyl group;

an aryl group which may be substituted with a halogen atom, an alkyl group or an alkoxy group; or an aralkyl group which may be substituted with a halogen atom, an alkyl group or an alkoxy group, or $R^6$ and $R^7$, or $R^6$ and $R^9$ are bonded to each other to form a $C_{2-4}$ alkylene group, provided that when $R^6$ and $R^9$ are the same group, $R^7$ and $R^8$ represent a different group.

The alkoxy groups substituted on the alkyl group may be bonded at their terminals to form an alkylene group such as an ethylene group, and specific examples of the ring formed by the alkoxy group and the alkyl group to which they are bonded include, for example, 1,3-dioxa-2-cyclopentyl group and the like.

Examples of the alkenyl group include, for example, a $C_{2-4}$ alkenyl group such as vinyl, propenyl, or butenyl group.

Examples of the alkoxycarbonyl group include, for example, those comprised of a carbonyl group and the alkoxy group as specified above (e.g. $C_{1-8}$ alkoxy group and preferably, a $C_{1-4}$ alkoxy group such as methoxy to butoxy group as specified above).

Examples of the halogenated alkoxycarbonyl group include, for example, a group comprised of the alkoxycarbonyl group as described above and a halogen atom, and specific examples thereof include a hexafluoroisopropoxycarbonyl group and the like.

The $C_{2-4}$ alkylene group represented by $R^6$ and $R^7$, or $R^6$ and $R^9$ means an ethylene, trimethylene, or tetramethylene group.

In the above reaction, the prochiral olefin (2) includes e.g. monolefins such as propene, 1-butene, isobutylene, 2-methyl-2-butene, 1,1,1-trichloro-4-methyl-3-pentene, 1,1,1-tribromo-4-methyl-3-pentene, 2-bromo-2,5-dimethyl-4-hexene, 2-chloro-2,5-dimethyl-4-hexene, 1-methoxy-2-methyl-1-propene, 1-ethoxy-2-methyl-1-propene, 1-propoxy-2-methyl-1-propene, 1-methoxy-3-methyl-2-butene, 1-ethoxy-3-methyl-2-butene, 1-propoxy-3-methyl-2-butene, 1,1-dimethoxy-3-methyl-2-butene, 1,1-diethoxy-3-methyl-2-butene, isopropylidene-cyclopropane, isopropylidene-cyclobutane, isopropylidene-cyclopentane and the like.

The prochiral olefin includes a conjugated diene such as 2,5-dimethyl-2,4-hexadiene,
2-chloro-5-methyl-2,4-hexadiene,
2-fluoro-5-methyl-2,4-dihexadiene,
1,1,1-trifluoro-2,5-dimethyl-2,4-hexadiene,
1,1-difluoro-4-methyl-1,3-pentadiene,
1,1-dichloro-4-methyl-1,3-pentadiene,
1,1-dibromo-4-methyl-1,3-pentadiene,
1-chloro-1-fluoro-4-methyl-1,3-pentadiene,
1-fluoro-1-bromo-4-methyl-1,3-pentadiene,
2-methoxycarbonyl-5-methyl-2,4-hexadiene,
2-hexafluoroisopropoxycarbonyl-5-methyl-2,4-hexadiene,
1-alkoxy(methoxy, ethoxy, or propxoy)-4-methyl-1,3-pentadiene,
1-fluoro-1-alkoxy(methoxy, ethoxyl, or propoxy)-4-methyl-1,3-pentadiene and the like. Preferable examples thereof include isobutylene, 2,5-dimethyl-2,4-hexadiene or the like.

The prochiral olefin is used usually in an amount at least 1 mol, preferably from 2 to 50 moles, per mol of the diazoacetate.

Examples of the diazoacetate include a diazoacetate of formula (3):

(3)

wherein $R^{10}$ represents a $C_{1-8}$ alkyl group;

a cycloalkyl group which may be substituted with an alkyl group;

a phenyl group which may be substituted with an alkyl group, an alkoxy group or a phenoxy group; or a benzyl group which may be substituted with an alkyl group, an alkoxy group or a phenoxy group.

Examples of the optically active cyclopropanecarboxylate include an optically active cyclopropanecarboxylate of formula (4):

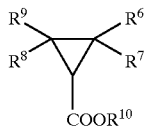

(4)

wherein $R^6$, $R^7$, $R^8$, $R^9$ and $R^{10}$ have the same meanings as defined above.

Preferred examples of $R^{10}$ include a methyl, ethyl, propyl, isopropyl, butyl, isobutyl, s-butyl, t-butyl, n-pentyl, n-hexyl, 1-menthyl, d-menthyl, benzyl, cyclohexyl, phenyl, m-methylphenyl, m-methoxyphenyl, m-phenoxyphenyl, 3,5-dimethylphenyl, 3,5-dimethoxyphenyl, 4-methyl-2,6-di-t-butylphenyl, or m-phenoxybenzyl group or the like.

The diazoacetate including the diazoacetate of formula (3) can be obtained by a method known in the art, and for example, it can be obtained by subjecting a corresponding amino acid ester to diazotization reaction and then extracting the product with a solvent such as chloroform, toluene, hexane, cyclohexane, heptane or the prochiral olefin. If necessary, the product can also be isolated by distillation or the like.

Examples of the solvent that may be used include, for example, a halogenated hydrocarbon such as 1,2-dichloroethane, chloroform, carbon tetrachloride, monochlorobutane or the like, an aliphatic hydrocarbon such as hexane, heptane, cyclohexane or the like, an aromatic hydrocarbon such as toluene, xylene or the like, an ester such as methyl acetate, ethyl acetate, methyl propionate, ethyl propionate or the like, the prochiral olefin (e.g. prochiral olefin of formula (2)), and a mixture thereof.

The solvent is used usually in an amount of 2 to 50 parts by weight, preferably 3 to 30 parts by weight per 1 part by weight of the diazoacetate.

An effective amount of the asymmetric copper complex catalyst can be used and it is preferably used in an amount of 0.0001 to 0.01 mol, more preferably from 0.0002 to about 0.005 mol per mol of the diazoacetate.

The asymmetric cyclopropanation reaction is usually conducted in an inert gas atmosphere such as nitrogen, argon or th like. The reaction temperature is usually −20 to 130° C., preferably −10 to about 110° C. The reaction may be conducted at a lower range to improve the selectivity of the reaction, typically in a prochiral olefin of lower-boiling point as a solvent, and the catalyst may be activated by adding a reducing agent such as phenylhydrazine prior to use, if necessary.

The reaction (asymmetric cyclopropanation) of the prochiral olefin with the diazoacetate in the presence of the asymmetric copper complex is typically conducted by adding the diazoacetate dissolved in a solvent to a mixture of the prochiral olefin and the asymmetric copper complex.

The asymmetric copper complex catalyst, the diazoacetate and/or the prochiral olefin may be continuously fed into a reaction vessel in the above temperature range, and the reaction solution containing the cyclopropanecarboxylate may be continuously withdrawn from the reaction vessel.

The optically active cyclopropanecarboxylate thus obtained in the reaction described above can be isolated by conventional techniques such as distillation or the like, and may be further purified by column chromatography or the like, if necessary.

Examples of the optically active cyclopropanecarboxylate (4) include, for example, optically active
2-methylcyclopropanecarboxylate,
2,2-dimethylcyclopropanecarboxylate,
2,2,3-trimethylcyclopropanecarboxylate,
2,2-dimethyl-3-(2,2,2-trichloroethyl) cyclopropanecarboxylate,
2,2-dimethyl-3-(2,2,2-tribromoethyl) cyclopropanecarboxylate,
2,2-dimethyl-3-(2-chloro-2-methyl) propylcyclopropanecarboxylate,
2,2-dimethyl-3-(2-bromo-2-methyl) propylcyclopropanecarboxylate,
2,2-dimethyl-3-methoxycyclopropanecarboxylate,
2,2-dimethyl-3-ethoxycyclopropanecarboxylate,
2,2-dimethyl-3-methoxymethylcyclopropanecarboxylate,
2,2-dimethyl-3-ethoxymethylcyclopropanecarboxylate,
2,2-dimethyl-3-propoxycyclopropanecarboxylate,
2,2-dimethyl-3-propoxymethylcyclopropanecarboxylate,
2,2-dimethyl-3-dimethoxymethylcyclopropanecarboxylate,
2,2-dimethyl-3-diethoxymethylcyclopropanecarboxylate,
2,2-dimethyl-3-(1,3-dioxa-2-cyclopentyl) cyclopropanecarboxylate,
2,2-dimethyl-3,3-cyclopropylidenecyclopropanecarboxylate,
2,2-dimethyl-3,3-cyclobutylidenecyclopropanecarboxylate,
2,2-dimethyl-3,3-cyclopentylidenecyclopropanecarboxylate and the like.

Among the optically active cyclopropanecarboxylates (4), those compounds substituted with an alkenyl include e.g. optically active ester compounds such as
2,2-dimethyl-3-(2-methyl-1-propenyl) cyclopropanecarboxylate,
2,2-dimethyl-3-(2-chloro-1-propenyl) cyclopropanecarboxylate,
2,2-dimethyl-3-(2-fluoro-1-propenyl) cyclopropanecarboxylate,
2,2-dimethyl-3-(2-chloro-2,2,2-trifluoromethylethenyl)-cyclopropanecarboxylate,
2,2-dimethyl-3-(2,2-difluoro-1-ethenyl) cyclopropanecarboxylate,
2,2-dimethyl-3-(2,2-dichloro-1-ethenyl) cyclopropanecarboxylate,
2,2-dimethyl-3-(2,2-dibromo-1-ethenyl) cyclopropanecarboxylate,
2,2-dimethyl-3-(2-fluoro-2-chloro-1-ethenyl) cyclopropanecarboxylate,
2,2-dimethyl-3-(2-fluoro-2-bromo-1-ethenyl) cyclopropanecarboxylate,
2,2-dimethyl-3-(2-methoxycarbonyl-1-propenyl) cyclopropanecarboxylate,
2,2-dimethyl-3-(2-hexafluoroisopropoxycarbonyl-1-propenyl)cyclopropanecarboxylate, 2,2-dimethyl-3-(2-alkoxy(methoxy, ethoxy, or propxoy)-1-ethenyl) cyclopropanecarboxylate,
2,2-dimethyl-3-(2-fluoro-2-alkoxy(methoxy, ethoxy, or propxoy)-1-ethenyl)cyclopropanecarboxylate and the like.

In the cyclopropanecarboxylates, preferable examples of the ester residues in the optically active cyclopropane compound (4) include, for example, a methyl, ethyl, n-propyl, i-propyl, i-butyl, t-butyl, cyclohexyl, menthyl, 4-methyl-2, 6-di-t-butylphenyl, or m-phenoxybenzyl group or the like.

The optically active cyclopropanecarboxylate thus obtained can be converted by ester hydrolysis in a known manner into its corresponding optically active cyclopropanecarboxylic acid wherein the substituent group $R^{10}$ is a hydrogen atom.

The method of this ester hydrolysis reaction is not particularly limited and can be conducted by a known method, for example by a method of hydrolysis with an alkali metal hydroxide, a method of elimination by decomposition under heating in the presence of an acid catalyst, etc.

EXAMPLES

Hereinafter, this invention is described in more detail by reference to the Examples but are not to be construed to limit the invention thereto.

Yield and optical purity were calculated according to the following equations:

Yield of cyclopropanecarboxylate (%)=$B \times 100/A$

Optical purity: (+)-trans isomer e.e. %=$(C-D) \times 100/(C+D)$ (+)-cis isomer e.e. %=$(E-F) \times 100/(E+F)$ wherein:
A=charged diazoacetate (mol);
B=cyclopropanecarboxylate (mol) formed after the reaction;
C=(+)-trans isomer;
D=(−)-trans isomer;
E=(+)-cis isomer; and
F=(−)-cis isomer.

Example 1A

After the atmosphere in a glass Schlenk tube having an internal volume of 50 ml was replaced by nitrogen, 9.8 mg (0.022 mmol) of 2,2'-isopylidenebis{(4R)-4-phenyl-5,5-diethyl-2-oxazoline}, 4 mg (0.02 mmol) of copper acetate monohydrate and 5 ml of ethyl acetate were added at room temperature, and after the mixture was stirred for 0.5 hour, 3.0 mg (0.02 mmol) of trifluoromethanesulfonic acid was added, and the mixture was stirred at room temperature for 1 hour to prepare a complex catalyst solution.

Example 1B 11 g (100 mmol) of 2,5-dimethyl-2,4-hexadiene was added to the complex catalyst prepared in Example 1A. Thereafter, 10 ml of a solution (containing 10 mmol ethyl diazoacetate) of ethyl diazoacetate in toluene was added thereto over 2 hours during which the reaction solution was kept at 20° C. Thereafter, the mixture was kept at 20° C. for 30 minutes. The yield of ethyl chrysanthemate as the product and the trans/cis isomer ratio were analyzed by GC, and the optical purity was analyzed by LC. The yield of ethyl chrysanthemate was 88.4% (relative to charged ethyl diazoacetate), trans/cis=74/26, the optical purity was 84% e.e. (trans) and 24% e.e. (cis).

Example 1C

The same reaction as in Example 1B was carried out except that t-butyl diazoacetate was used in place of ethyl diazoacetate in Example 1B. After the product was converted into a 1-menthyl derivative, the optical purity was analyzed by GC.

The yield of t-butyl chrysanthemate was 81.5% (relative to charged t-butyl diazoacetate), trans/cis=83/17, and the optical purity was 94% e.e. (trans), and 60% e.e. (cis).

Example 2A

A complex catalyst was prepared in a similar manner as in Example 1A except that the amount of trifluoromethanesulfonic acid added in Example 1A was changed to 6.0 mg (0.04 mmol).

Example 2B

The same reaction as in Example 1B was carried out except that the complex catalyst prepared in Example 2A was used in Example 1B.

The yield of ethyl chrysanthemate was 89.2% (relative to charged ethyl diazoacetate), trans/cis=74/26, and the optical purity was 85% e.e. (trans), and 25% e.e. (cis).

Example 3A

A complex catalyst was prepared in a similar manner as in Example 1A except that 2.8 mg (0.02 mmol) of boron trifluoride-diethyl ether complex was used in place of trifluomethanesulfonic acid in Example 1A.

Example 3B

The reaction was carried out in a similar manner as in Example 1B except that the complex catalyst prepared in Example 3A was used in Example 1B.

The yield of ethyl chrysanthemate was 90.3% (relative to charged ethyl diazoacetate), trans/cis=74/26, and the optical purity was 85% e.e. (trans), and 33% e.e. (cis).

Example 4A

A complex catalyst was prepared in a similar manner as in Example 1A except that 4 mg (0.04 mmol) of fluorosulfonic acid was used in place of trifluomethanesulfonic acid in Example 1A.

Example 4B

The reaction was carried out in a similar manner as in Example 1B except that the complex catalyst prepared in Example 4A was used in Example 1B.

The yield of ethyl chrysanthemate was 87.9% (relative to charged ethyl diazoacetate), trans/cis=72/28, and the optical purity was 82% e.e. (trans), and 29% e.e. (cis).

Example 5A

A complex catalyst was prepared in a similar manner as in Example 1A except that 2 mg (0.02 mmol) of fluorosulfonic acid and 2.8 mg (0.02 mmol) of boron trifluoride-methanol complex were used in place of trifluomethanesulfonic acid in Example 1A.

Example 5B

The reaction was carried out in a similar manner as in Example 1B except that the complex catalyst prepared in Example 5A was used in Example 1B.

The yield of ethyl chrysanthemate was 88.9% (relative to charged ethyl diazoacetate), trans/cis=74/26, and the optical purity was 84% e.e. (trans), and 33% e.e. (cis).

Example 6A

A complex catalyst was prepared in a similar manner as in Example 1A except that 2 mg (0.02 mmol) of fluorosulfonic acid and 4.3 mg (0.02 mmol) antimony pentafluoride were used in place of trifluomethanesulfonic acid in Example 1A.

Example 6B

The reaction was carried out in a similar manner as in Example 1B except that the complex catalyst prepared in Example 6A was used in Example 1B.

The yield of ethyl chrysanthemate was 90.7% (relative to charged ethyl diazoacetate), trans/cis=74/26, and the optical purity was 85% e.e. (trans), and 38% e.e. (cis).

Example 7A

A complex catalyst was prepared in a similar manner as in Example 1A except that 4 mg (0.04 mmol) of fluorosulfonic acid and 8.6 mg (0.04 mmol) of antimony pentafluoride were used in place of trifluomethanesulfonic acid in Example 1A.

Example 7B

The reaction was carried out as in Example 1B except that the complex catalyst prepared in Example 7A was used in Example 1B.

The yield of ethyl chrysanthemate, 93.2% (relative to charged ethyl diazoacetate), trans/cis=75/25, and the optical purity was 86% e.e. (trans), and 40% e.e. (cis).

Example 8A

A complex catalyst was prepared in a similar manner as in Example 1A except that 2.0 mg (0.02 mmol) of cuprous chloride was used in place of copper acetate monohydrate in Example 1A.

Example 8B

The reaction was carried out in a similar manner as in Example 1B except that the complex catalyst prepared in Example 8A was used in Example 1B.

The yield of ethyl chrysanthemate was 88.3% (relative to charged ethyl diazoacetate), trans/cis=74/26, and the optical purity was 84% e.e. (trans), and 25% e.e. (cis).

Example 9A

A complex catalyst was prepared in a similar manner as in Example 1A except that 10.1 mg (0.022 mmol) of 2,2'-methylenebis{(4R,5S)-4,5-diphenyl-2-oxazoline} was used in place of 2,2'-isopylidenebis{(4R)-4-phenyl-5,5-diethyl-2-oxazoline} in Example 1A.

Example 9B

The reaction was carried out in a similar manner as in Example 1B except that the complex catalyst prepared in Example 9A was used in Example 1B. The yield of ethyl chrysanthemate was 84.1% (relative to charged ethyl diazoacetate), trans/cis=73/27, and the optical purity was 70% e.e. (trans), and 35% e.e. (cis).

Example 10A

A complex was prepared in a similar manner as in Example 9A except that 53 mg (0.1 mmol) of tris-(pentafluorophenyl)aluminium was used in place of trifluoromethanesulfonic acid.

Example 10B

The reaction was carried out in a similar manner as in Example 1B except that the complex catalyst prepared in Example 10A was used. The yield of ethyl chrysanthemate was 95.9% (relative to charged ethyl diazoacetate), trans/cis=69/31, and the optical purity was 54% e.e. (trans), and 35% e.e. (cis).

Example 11A

A complex catalyst was prepared in a similar manner as in Example 1A except that 6.5 mg (0.022 mmol) of 2,2'-isopylidenebis{(4R)-4-t-butyl-2-oxazoline} was used in place of 2,2'-isopylidenebis{(4R)-4-phenyl-5,5-diethyl-2-oxazoline} in Example 1A.

Example 11B 1.25 ml of complex catalyst solution (containing 0.005 mmol Cu) prepared in Example 11A, 5 ml of ethyl acetate, 3.4 g (60 mmol) of isobutylene were added to a 100-ml autoclave of which atmosphere had been replaced by nitrogen. Thereafter, 20 ml of a solution (containing 20 mmol ethyl diazoacetate) of ethyl diazoacetate in toluene was fed thereto over 2 hours during which the reaction solution was kept at 40° C. Thereafter, the mixture was kept at 40° C. for 30 minutes. The yield of the product ethyl cyclopropanecarboxylate was analyzed by GC, and after conversion of the product into 1-menthyl derivative, the optical purity was analyzed by GC. The yield of ethyl cyclopropanecarboxylate was 98% (relative to charged ethyl diazoacetate), and the optical purity was 96% e.e. (+).

Example 12A

A complex catalyst was prepared in a similar manner as in Example 1A except that 2.8 mg (0.02 mmol) of boron trifluoride-diethyl ether complex was used in place of trifluoromethanesulfonic acid in Example 11A.

Example 12B

The reaction was carried out in a similar manner as in Example 11B except that the complex catalyst prepared in Example 12A was used in Example 11B. The yield of ethyl cyclopropanecarboxylate was 98% (relative to charged ethyl diazoacetate), and the optical purity was 96% e.e. (+).

Example 13A

After the atmosphere in a glass Schlenk tube having an internal volume of 50 ml was replaced by nitrogen, 4 mg (0.02 mmol) of copper acetate monohydrate and 5 ml of ethyl acetate were added at room temperature, and 3.0 mg (0.02 mmol) of trifluoromethanesulfonic acid was added, and after mixture was stirred for 0.5 hour, 6.5 mg (0.022 mmmol) of 2,2'-isopylidenebis{(4S)-4-t-butyl-2-oxazoline} was added, and the mixture was stirred at room temperature for 1 hour to prepare a complex catalyst solution.

Example 13B

The reaction was carried out in a similar manner as in Example 11B except that the complex catalyst prepared in Example 13A was used in Example 11B. The yield of ethyl cyclopropanecarboxylate was 98% (relative to charged ethyl diazoacetate), and the optical purity was 96% e.e. (−).

Example 14A

After the atmosphere in a glass Schlenk tube having an internal volume of 50 ml was replaced by nitrogen, 6.5 mg (0.022 mmol) of 2,2'-isopylidenebis{(4S)-4-t-butyl-2-oxazoline} and 5 ml of ethyl acetate were added at room temperature, and 3.0 mg (0.02 mmol) of trifluoromethanesulfonic acid was added, and after the mixture was stirred for 0.5 hour, 4 mg (0.02 mmol) of copper acetate monohydrate was added, and the mixture was stirred at room temperature for 1 hour to prepare a complex catalyst solution.

Example 14B

The reaction was carried out in a similar manner as in Example 11B except that the complex catalyst prepared in Example 14A was used in Example 11B. The yield of ethyl cyclopropanecarboxylate was 98% (relative to charged ethyl diazoacetate), and the optical purity was 96% e.e. (−).

What is claimed is:

1. An asymmetric copper catalyst composition comprising, as components,
   (a) an optically active bisoxazoline compound of formula (1):

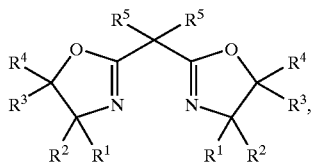

(1)

wherein
   $R^1$ and $R^2$ are different and each represents:
   a hydrogen atom, an alkyl group, a cycloalkyl group, or a phenyl or aralkyl group which may be substituted; $R^3$ and $R^4$ each represents a hydrogen atom, an alkyl group, a cycloalkyl group, or a phenyl or aralkyl group which may be substituted, or $R^3$ and $R^4$ are bonded to each other to form a $C_{3-5}$ cyclic alkylene group; and
   $R^5$ represents a hydrogen atom or a $C_{1-6}$ alkyl group, or the two $R^5$ groups are bonded to each other to represent a $C_{3-6}$ cyclic alkylene group;
   (b) a monovalent or divalent copper compound; and
   (c) a Lewis acid or a mixture of the Lewis acid and a strong acid that is selected from the group consisting of fluorosulfonic acid, chlorosulfonic acid, hydrogen fluoride, fuming sulfuric acid, and concentrated sulfuric acid.

2. An asymmetric copper catalyst composition according to claim 1, wherein the monovalent or divalent a copper compound is copper $C_{2-15}$ organic carboxylate, copper acetylacetonate, copper chloride, copper bromide, copper methanesulfonate, copper carbonate, copper oxide, or copper hydroxide.

3. A process for producing the asymmetric copper catalyst composition as defined in claim 1, which comprises mixing
   (a) an optically active bisoxazoline compound of formula (1) as defined in claim 1,
   (b) a monovalent or divalent copper compound, and
   (c) a Lewis acid or a mixture of the Lewis acid and a strong acid that is selected from the group consisting of fluorosulfonic acid, chlorosulfonic acid, hydrogen fluoride, fuming sulfuric acid, and concentrated sulfuric acid.

4. An asymmetric copper catalyst composition according to claim 1, wherein the Lewis acid is boron trifluoride, tantalum pentafluoride, niobium pentafluoride, titanium tetrafluoride, phosphorus pentafluoride, antimony pentafluoride, arsenic pentafluoride, tungsten hexafluoride, antimony trifluoride, aluminum trifluoride, a boron trifluoride-diethyl ether complex, a boron trifluoride-methanol complex, or a boron trifluoride-phenol complex.

5. An asymmetric copper catalyst composition according to claim 2, wherein the mixture of a strong acid and a Lewis acid is
   a mixture of boron trifluoride and hydrogen fluoride,
   a mixture of antimony pentafluoride and hydrogen fluoride,
   a mixture of phosphorus pentafluoride and hydrogen fluoride, or
   a mixture of antimony pentafluoride and fluorosulfonic acid.

6. An asymmetric copper catalyst composition according to claim 1, wherein the amount of the optically active bisoxazoline compound of formula (1) is 0.9 to 2 moles per mol of the monovalent or divalent copper compound, and the amount of the Lewis acid or the mixture of the strong acid with the Lewis acid is 0.3 to 5 moles per mol of the monovalent or divalent copper compound.

7. A composition according to claim 1, which further comprises an organic solvent.

8. An asymmetric copper catalyst composition comprising, as components,
   (a) an optically active bisoxazoline compound of formula (1):

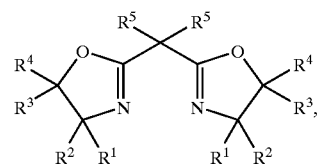

(1)

wherein
   $R^1$ and $R^2$ are different and each represents:
   a hydrogen atom, an alkyl group, a cycloalkyl group, or a phenyl or aralkyl group which may be substituted; $R^3$ and $R^4$ each represents a hydrogen atom, an alkyl group, a cycloalkyl group, or a phenyl or aralkyl group which may be substituted, or $R^3$ and $R^4$ are bonded to each other to form a $C_{3-5}$ cyclic alkylene group; and
   $R^5$ represents a hydrogen atom or a $C_{1-6}$ alkyl group, or the two $R^5$ groups are bonded to each other to represent a $C_{3-6}$ cyclic alkylene group;
   (b) a monovalent or divalent copper compound; and
   (c) a Lewis acid.

9. A process for producing the asymmetric copper catalyst composition as defined in claim 8, which comprises mixing
   (a) an optically active bisoxazoline compound of formula (1) as defined in claim 8,
   (b) a monovalent or divalent copper compound, and
   (c) a Lewis acid.

10. An asymmetric copper catalyst composition according to claim 8, which further comprises an organic solvent.

11. An asymmetric copper catalyst composition according to claim 8, wherein the amount of the optically active bisoxazoline compound of formula (1) is 0.9 to 2 moles per mol of the monovalent or divalent copper compound, and the amount of the Lewis acid is 0.3 to 5 moles per mol of the monovalent or divalent copper compound.

12. An asymmetric copper catalyst composition according to claim 8, wherein the monovalent or the divalent copper compound is copper $C_{2-15}$ organic carboxylates, copper acetylacetonate, copper chloride, copper bromide, copper methanesulfonate, copper carbonate, copper oxide, or copper hydroxide.

13. An asymmetric copper catalyst composition according claim 8, wherein the Lewis acid is boron trifluoride, tantalum pentafluoride, niobium pentafluoride, titanium tetrafluoride, phosphorus pentafluoride, antimony pentafluoride, arsenic pentafluoride, tungsten hexafluoride, antimony trifluoride, aluminum trifluoride, a boron trifluoride-diethyl ether complex, a boron trifluoride-methanol complex, or a boron trifluoride-phenol complex.

* * * * *